United States Patent [19]
Imperiali et al.

[11] Patent Number: 6,083,758
[45] Date of Patent: *Jul. 4, 2000

[54] METHOD FOR SCREENING PEPTIDES FOR METAL COORDINATING PROPERTIES AND FLUORESCENT CHEMOSENSORS DERIVED THEREFROM

[75] Inventors: Barbara Imperiali; Grant K. Walkup, both of Pasadena, Calif.

[73] Assignee: California Institute of Technology, Pasadena, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/831,626

[22] Filed: Apr. 9, 1997

[51] Int. Cl.[7] .......................... G01N 33/20; G01N 33/552

[52] U.S. Cl. .................. 436/73; 436/81; 436/85; 436/86; 436/527; 436/530; 436/533; 436/534

[58] Field of Search .................. 436/73, 79–81, 436/85, 530, 533–34, 86, 527

[56] References Cited

U.S. PATENT DOCUMENTS 5,679,548  10/1997  Barbas et al. .......................... 435/69.6

OTHER PUBLICATIONS

Gallop et al., "Application of Combinatorial Technologies to Drug Discovery. 1. Background and Peptide Conbinatorial Lobraries", J. of Med. Chem., vol. 37, No. 9, pp. 1233–1251, Apr. 29, 1994.

Sasaki et al., "Metal Induced Dispersion of Lipid Aggregates: A Simple, Selective, and Sensitive Fluorescent Metal Ion Sensor", Angew. Chem. Int. Ed. Eng., 1995, 34 No. 8., pp. 905–907.

Fabbrizzi et al., "An Anthracene–Based Fluorescent Sensor for Transition Metal Ions", Angew. Chem. Int. Ed. Engl. 1994, 33, No. 19, pp.1975–1977.

Fabbrizzi et al., "Fluorescent Sensors for Transition Metals Based on Electron–Transfer and Energy–Transfer Mechanisms", Chem. Eur. J. 1996, 2, No. 1, pp. 75–82.

Santis et al., A Fluorescent Chemosensor for the Copper (II) Ion, Inorganic Chimica Acta 257 (1997), pp. 69–76.

Minta, A.; Tsien, R. Y. "Fluorescent Indicators for Cytosolic Sodium," J. Biol. Chem. 1989, 264, 19449.

Tsien, R. Y. "New Calcium Indicators and Buffers with High Selectivity against Magnesium and Protons: Design, Synthesis, and Properties of Prototype Structures,"Biochemistry 1980, 19, 2396.

Grynkiewica, G; Poenie, M.; Tsien, R. Y. "A New Generation of $Ca^{2+}$ Indicators with Greatly Improved Fluorescence Properties," J. Biol. Chem. 1985, 260, 3440.

Raju, B.; Murphy, E.; Levy, L. A., et al. "A fluorescent indicator for measuring cytosolic free magnesium," Am. J. Physiol. 1989, 256, C540.

Bassnett, S.; Reinisch, L.; Beebe, D. C. "Intracellular pH measurement using single excitation–dual emission fluorescence ratios" Am. J. Physiol. 1990, 258, C171.

Rink, T.J.; Tsien, R. Y.; Pozzan, T. "Cytoplasmic pH and Free $Mg^{2+}$ in Lymphocytes" Cell Biol. 1982, 95, 189.

Czarnik, A. W. "Supramolecular Chemistry, Fluorescence, and Sensing" In "Fluorescent Chemosensors for Ion and Molecular Recognition", Czamik, ed., ACS, Washington D.C., 1993; pp 1.

Giuliano, K. A.; Post, P. L.; Hahn, K. M., et al. "Fluorescent Protein Biosensors: Measurement of Molecular Dynamics in Living Cells" Ann. Rev. Biophys. Biomol. Struct. 1995, 24, 405.

Thompson, R.B; Jones, E.R. "Enzyme–Based Fiber Optic Zinc Biosensor"Anal. Chem. 1993, 65, 730.

(List continued on next page.)

Primary Examiner—Lyle A. Alexander
Attorney, Agent, or Firm—Brinks, Hofer, Gilson & Lione

[57] ABSTRACT

Methods for identifying polypeptides which coordinate to select metals, chemosensors comprising polypeptides which coordinate to select metals and methods for selectively detecting the presence of metals using these chemosensors are disclosed.

10 Claims, 6 Drawing Sheets

OTHER PUBLICATIONS

Thompson, R.B.; Patchan, M.W. "Lifetime–Based Fluorescence Energy Transfer Biosensing of Zinc," *Anal. Biochem.* 1995, 227, 123.

Virta, M.; Lampinen, J.; Karp, M. "A Luminsecence–based Mercury Biosensor," *Anal. Chem.* 1995, 67, 667.

Thompson, R. B.; Ge, Z.; Patchan, M., et al. "Fiber optic biosensor for Co(II) and Cu(II) based on fluorescence energy transfer with an enzyme transducer," *Biosensors & Bioelectronics* 1996, 11, 557.

Adams, S.R.; Harootunian, A. T.; Buechler, Y. J., et al. "Fluorescence ratio imaging of cyclic AMP in single cells," *Nature* 1991, 349, 694.

Czarnik, A. W. "Desperately seeking sensors," *chem. Bio.* 1995, 2, 423.

Cheng, R. P.; Fisher, S. L.; Imperiali, B. "Metallopeptide Design: Tuning the Metal Cation Affinities with Unnatural Amino Acids and Peptide Secondary Structure," *J. Am. Chem. Soc.* 1996, 118, 11349.

Torrado, A.; Imperiali, B. "New Synthetic Amino Acids for the Deisgn and Synthesis of Peptide–Based Metal Ion Sensors," *J. Org. Chem.* 1996, 61, 8940.

Walkup, G. K.; Imperiali, B. "Design and Evaluation of a Peptidyl Fluorescent Chemosensor for Divalent Zinc," *J. Am. Chem. Soc.* 1996, 118, 3053.

Berg, J.M.; Merkle, D. L. "On the Metal Ion Specificity of 'Zinc Finger' Proteins," *J. Am. Chem. Soc.* 1989, 111, 3759.

Krizek, B. A.; Merkle, D. L.; Berg, J. M. "Ligand Variation and Metal Ion Binding Specificity in Zinc Finger Peptides," *Inorg. Chem.* 1993, 32, 937.

Krizek, B. A.; Berg, J. M. "complexes of Zinc Finger Peptides with $Ni^{2+}$ and $Fe^{2+}$," *Inorg. Chem.* 1992, 31, 2984.

Berg, J. M. "Zinc Finger Domains: From Predictions to Design," *Acc. Chem. Res.* 1995, 28, 14.

Klug, A.; Schwabe, J. W. R. "Protein Motifs 5: Zinc Fingers," *FASEB J.* 1995, 9, 597.

Eis, P.S.; Lakowicz, J. R. "Time–Resolved Energy Transfer Measurements of Donor–Acceptor Distance Distributions and Intramolecular Flexibility of a CCHH Zinc Finger Peptide," *Biochemistry* 1993, 32, 7981.

Frankel, A. D.; Berg, J. M.; Pabo, C. O. "Metal–dependent folding of a single zinc finger from transcription factor IIIA," *Proc. Natl. Acad. Sci. U.S.A.* 1987, 84, 4841.

Godwin, H. A.; Berg, J. M. "A Fluorescent Zinc Probe Based on Metal–Induced Peptide Folding," *J. Am. Chem. Soc.* 1996, 118, 6514.

Sundberg, S. A.; Barrett, R. W.; Pirrung, M., et al. "Spatially–Addressable Immobilization of Macromolecules on Solid Supports," *J. Am. Chem. Soc.* 1995, 117, 12050.

Holmes, C. P.; Adams, C. L.; Kochersperger, L. M., et al. "The Use of Light–Directed Combinatorial Peptide Synthesis in Epitope Mapping," *Biopolymers (Peptide Science)* 1995, 37, 199.

Fodor, S. P. A.; Read, J. L.; Firrung, M.C., et al. "Light–Directed Spatially Addressable Parallel Chemical Synthesis," *Science* 1991, 251, 767.

Haughland, R. P.; "Covalent Fluorescent Probes," In *Excited states of biopolymers*; Steiner, R.F., ed., Plenum Press, New York, 1983; pp 29.

Krizek, B. A.; Amann, B. T.; Kilfoil, V. J., et al. "A consensus Zinc Finger Peptide: Design, High–Affinity Metal Binding, a pH–Dependent Structure, and a His to Cys Sequence Variant," *J. Am. Chem. Soc.* 1991, 113, 4518.

Jacobs, G. H. "Determination of the base recognition positions of zinc fingers from sequence analysis," *EMBO J.* 1992, 11, 4507.

Berg, J. M. "Zinc Finger Domains: Hypothesis and Current Knowledge," *Annual Reviews of Biophysics and Biophysical Chemistry* 1990, 19, 405.

Berg, J. M. "Zinc–finger Proteins," *Curr. Opin. Struct. Biol.* 1993, 3, 11.

Klevit, R. E.; Herriott, J. R.; Horvath S. J. "Solution Structure of a Zinc Finger Domain of Yeast ADR1," *Proteins: Struct. Func. Gen.* 1990, 7, 215.

Pavletich, N. P.; Pabo, C. O. "Zinc Finger–DNA Recognition: Crystal Structure of a Zif268–DNA Complex at 2.1 Å," *Science* 1991, 252, 809.

Fairall, L.; Schwabe, J. W. R.; Chapman, L., et al. "The crystal structure of two zinc finger peptides reveals and extension to the rules for zinc finger/DNA recognition," *Nature* 1993, 366, 483.

Lakowicz, J. R.; "Effects of Solvents on Fluorescence Emission Spectra," In *Principles of Fluorescence Spectroscopy*, Plenum Press. New York, 1983; p 187.

Mukherhee, G. N.; Chattopadhyay, S. K. "Metal Complexes of some Model Peptide Derivatives. Part–IX. Complexation Equilibria of Cobalt–, Nickel–, Copper– and Zinc(II) with Salicyloylglycylglycine," *J. Indian Chem. Soc.* 1991, 68, 639.

Hulsbergen, F. B.; Reedijk, J. "Coordination compounds of tripeptides and pentapeptides containing L–histidyl residues," *Recl. Trav. Chim. Pays–Bas* 1993, 112, 278.

Ama, T.; Kawagughi, Uchijma, M., et al. "Metal Complexes of Peptides. IV. Cobalt(III) Complexes with β–Alanyl–L–histidine (Carnosine) Functioning as a Quadridentate Ligand," *Bull. Chem. Soc. Jpn.* 1989, 62, 3464.

Patchornik, A.; Amit, B.; Woodward, R. B. "Photosensitive Protecting Groups," *J. Am. Chem. Soc.* 1970, 92, 6333.

Amit, B.; Zehavi, U.; Patchornik, A. "Photosensitive Protecting Groups of Amino Sugars and Their Use in Glucoside Synthesis. 2–Nitrobenzyloxycarbonylamino and 6–Nitroveratryloxycarbonylamino Derivatives," *J. Org. Chem.* 1974, 39, 192.

Flanders, D. C.; Smith, H. I.; Austin, S. "A new interferometric alignment technique," *Appl. Phys. Lett.* 1977, 31, 426.

Pless, J.; Bauer, W. "Boron Tris(trifluoroacetate) for Removal of Protecting Groups in Peptide Chemistry," *Angew. Chem. Int. Ed. Engl.* 1973, 12, 147.

Muller–Ackermann, E.; Panne, U.; Niessner, R. "A Fiber Optic Sensor Array for the Fluorimetric Detection of Heavy Metals," *Anal. Meth. I.* 1995, 2, 182.

Camerman, N.; Camerman, A.; Sarkar, B. "Molecular design to mimic the copper(II) transport site of human albumin. The crystal and molecular structure of copper (II)—glycylglycyl–L–histidine–N–methyl amide monoaquo complex," *Can. J. Chem.* 1976, 54, 1309.

Hay, R. W.; Hassan, M. M.; You–Quan, C. "Kinetic and Thermodynamic Studies of Copper(II) and Nickel(II) Complexes of Glycylglycyl–L–Histidine," *J. Inorg. Bioch.* 1993, 52, 17.

Shullenberger, D. F.; Eason, P. D.; Long, E. C. "Design and Synthesis of a Versitile DNA–Cleaving Metallopeptide Structural Domain," *J. Am. Chem. Soc.* 1993, 115, 11038.

Walkup, G.K., Imperiali, B., *J. Am. Chem. Soc.* 1997, in press.

1 n=3  Lys-Gly-His-Ser-Ser-SerCONH₂
2 n=2  Orn-Gly-His-Ser-Ser-SerCONH₂
3 n=1  Amb-Gly-His-Ser-Ser-SerCONH₂
4 n=0  Baa-Gly-His-Ser-Ser-SerCONH₂

Array of sensing peptides. Each array element may be a different peptide, or duplicate array elements may be fabricated by choice.

NOTE: Substrate for array and recording/detecting equipment not drawn to scale.

Example of readout, with array elements 2, 9, 11, and 12 showing varying signal intensity.

METHOD FOR SCREENING PEPTIDES FOR METAL COORDINATING PROPERTIES AND FLUORESCENT CHEMOSENSORS DERIVED THEREFROM

The U.S. Government has certain rights in this invention pursuant to Grant No. CHE-9522179 awarded by the National Science Foundation.

BACKGROUND OF THE INVENTION

1. Field of the Invention

This invention provides methods for identifying polypeptides which selectively coordinate to metals. This invention also provides chemosensors comprising polypeptides which coordinate to metals and methods for detecting the presence of metals using these chemosensors.

2. Background of the Invention

Fluorescent indicators have revolutionized the process of quantifying metal cations in aqueous media, and in particular within biological samples. The success of fluorescent indicators for the intracellular measurement of sodium and potassium (Minta, A.; Tsien, R. Y., *J. Biol. Chem.* 1989, 264:19449–19457), calcium (Tsien, R. Y., *Biochemistry* 1980, 19:2396–2404; Grynkiewicz, G., et al., *J. Biol. Chem.* 1985, 260:3440–3450), magnesium (Raju, B., et al., *Am. J. Physiol.* 1989, 256: C540), and pH (Bassnett, S., et al., *Am. J. Physiol.* 1990, 258: C171–C178; Rink, T. J., et al., *Cell Biol.* 1982, 95:189–196) is well known. Due to the success of these agents, the design and production of fluorescent chemosensors for other species continues to be an active area of interest.

The central problem in the production of new fluorescent sensors for the detection of metal cations lies in selectivity (Czarnik, A. W., Supramolecular Chemistry, Fluorescence, and Sensing. In *Fluorescent Chemosensors for Ion and Molecule Recognition*; Czarnik, A. W.; ACS, Washington, D.C., 1993; pp. 1–9). In fact, there are successful intracellular fluorescent probes only for the divalent cations $Mg^{2+}$ and $Ca^{2+}$, which are present at the highest concentration within the cell. For example, the concentration of ionized $Zn^{2+}$ within a cell or in sea water may be as much as $10^6$ fold less concentrated than that of $Mg^{2+}$ or $Ca^{2+}$ (Bruland, K. W., Trace Elements in Sea Water. In Rilet, J. P.; Chester, R.; Academic Press, London, 1975; pp. 157–220; Frausto da Silva, J. J. R.; Williams, R. J. P., *The Biological Chemistry of the Elements: The Inorganic Chemistry of Life*; Clarendon Press: New York, 1993.). Thus, the fluorescent indicator fura-2 may bind $Zn^{2+}$ with greater affinity than $Ca^{2+}$, but remains a cellular probe for free calcium. In order to prevent spurious cross-talk, the relative affinity of the sensor for the ion of interest must exceed the cumulative concentration excess imposed by all other competing species. Typically, this difficulty has been addressed by the exploitation of proteins for their unmatched selectivity in binding small molecules (Giuliano, K. A., et al., *Ann. Rev. Biophys. Biomol Struct.* 1995, 23:405–434). Thus biological signal transducers, i.e. "biosensors," have been devised from existing proteins for the divalent cations of zinc (Thompson, R. B., *Anal. Chem.* 1993, 65:730–734; Thompson, R. B.; Patchan, M. W., *Anal. Biochem.* 1995, 227:123–128), mercury (Virta, J.; Lampinen, J.; Karp, M., *Anal. Chem.* 1995, 67:667–669), as well as copper and cobalt (Thompson, R. B., et al., *Biosensors & Bioelectronics* 1996, 11:557–564), and even organic molecules such as cAMP (Adams, S. R., et al., *Nature* 1991, 694–697).

Nonetheless, the need for new chemosensors for these and other analytes continues to exist (Czarnik, A. W., *Chem. Bio.* 1995, 2:423–428). Although the analyte binding selectivity which may be obtained with a biosensor is remarkable, the complexity of a large biomolecule can impose greater design constraints relative to an abiotic sensing molecule. For example, proteins typically lack the fluorescence characteristics of a useful sensor, and thus a strategy involving affinity labeling or an auxiliary diffusible fluorophore is required for signal transduction. In this light, the production of a purely synthetic chemosensor is desirable as there is greater flexibility for systematic variation of the analyte-binding and fluorescent moieties of the sensor. The production of peptidyl motifs with tunable metal binding properties (Cheng, R. P., et al., *J. Am. Chem. Soc.* 1996, 118:11349–11356), as well as those with novel fluorescent signaling capabilities (Torrado, A.; Imperiali, B., *J. Org. Chem.* 1996, 61:8940–8948) highlights the applicability of this technique.

Previously, the present inventor has investigated the production of zinc-sensing fluorosensors using a hybrid approach (Walkup, G. K.; Imperiali, B., *J. Am. Chem. Soc.* 1996, 118:3053–3054). By exploiting the selective metal binding properties of the zinc finger domains (Berg. J. M.; Merkle, D. L., *J. Am. Chem. Soc.* 1989, 111:3759–3761), the advantageous aspects of abiotic chemosensors and biosensors have been combined within a synthetic polypeptide architecture. Zinc finger peptides bind divalent zinc avidly, with dissociation constants as low as 5.7 pM reported for the peptide·$Zn^{2+}$ complex (Krizek, B. A.; Merkle, D. L.; Berg, J. M., *Inorg. Chem.* 1993, 32:937–940), and with great selectivity (Krizek, B. A.; Berg, J. M., *Inorg. Chem.*, 1992, 31:2984–2986).

A single zinc finger domain is 25–30 residues in length and may be described by the consensus sequence

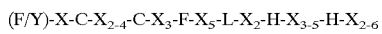

where X is any amino acid (Berg, J. M., *Acc. Chem. Res.* 1995, 28:14–19; Klug, A.; Schwabe, J. W. R., *FASEB J.* 1995, 9:597–604). Importantly, peptides of these lengths are synthetically accessible by chemical techniques. Furthermore, zinc fingers have been shown to undergo a reversible metal-induced conformational change (Eis, P. S.; Lakowicz, J. R., Biochemistry 1993, 32:7981–7993; Frankel, A. D., et al., *Proc. Natl. Acad Sci. U.S.A.* 1987, 84:4841–4845), which nucleates a cluster of hydrophobic residues (underlined above).

The present inventor reported the synthesis and characterization of a fluorescent synthetic peptidyl chemosensor for divalent zinc, patterned after the zinc fingers (Walkup, 1996, supra; Walkup, G. K., Imperiali, *J. Am. Chem. Soc.* 1997, in press). An aromatic residue of the hydrophobic cluster of the parent sequence was replaced with a derivative of β-amino alanine, incorporating an orthogonally protected side-chain amine. At the completion of the peptide synthesis, this residue was selectively deprotected, then coupled with a variety of amine-reactive fluorophores to produce a selectively labeled fluorescent peptide. Deprotection and cleavage of the peptide from the synthesis resin afforded the completed chemosensor. The microenvironment experienced by the fluorophore-bearing residue changed upon peptide·$Zn^{2+}$ complex formation, resulting in enhanced fluorescence. In addition, the subsequent report of another sensor developed along similar lines was noted (Godwin, H. A.; Berg, J. M., *J. Am. Chem. Soc.* 1996, 118:6514–6515), but which uses two fluorophores and a resonant energy transfer mechanism for signal transduction.

Both of these sensors are capable of quantifying nanomolar concentrations of $Zn^{2+}$, but are susceptible to oxidation through the formation of an intramolecular disulfide bond and are thus incompatible with aqueous oxidants including oxygen and redox active ions such as $Cu^{2+}$. This may not be problematic in the reducing environment of a cell, but application of these sensors toward the measurement of environmental samples would be precluded.

Despite these and other advances, chemosensors with broader applicability, increased selectivity and increased sensitivity are desirable.

SUMMARY OF THE INVENTION

Accordingly, one object of this invention is to provide methods for identifying polypeptides which coordinate to select metals.

A second object of this invention is to provide chemosensors comprising polypeptides which coordinate to select metals.

A third object of this invention is to provide methods for detecting the presence of a metal in a biological or environmental sample.

The present inventor has now developed a method of screening peptides for metal coordinating properties which combines combinatorial synthesis and fluorescent detection. This is most conveniently achieved by synthesizing a library of peptides on a solid support and subjecting the support to fluorescence analysis in the presence of various metal ions. Two signaling mechanisms will be employed. For sensors of Mechanism type A (FIG. 1) the fluorescence would be decreased due to intramolecular energy transfer from the fluorphore to the bound metal ion. For sensors of Mechanism type B (FIG. 1) the fluorescence would be increased due to the sequestration of the fluorophore into the hydrophobic environment of the metal bound (and folded) polypeptide.

These and other aspects and features of the invention will become more fully understood in the following detailed description.

DETAILED DESCRIPTION OF ILLUSTRATED EMBODIMENTS

1. Method of Screening for Peptides with Metal Coordinating Properties

1A. Peptides

Suitable chemosensor peptides with the present invention contain at least one metal coordinating group. As used herein, "metal coordinating groups" include both metal binding and metal signaling groups. The peptides are composed of at least three amino acid residues, preferably at least six amino acid residues. The peptides can be of any length. Preferably, the peptides are composed of at most 15, more preferably 10 residues.

Suitable amino acids include the naturally encoded amino acids such as alanine (Ala, A), arginine (Arg, R), asparagine (Asn. N), aspartic acid (Asp, D), cysteine (Cys, C), glutamine (Gin, Q), glutamic acid (Glu, E), glycine (Gly, G), histidine (His, H), isoleucine (Ile, I), leucine (Leu, L), lysine (Lys, K), methionine (Met, M), ornithine (Orn, O), phenylalanine (Phe, F), proline (Pro, P), serine (Ser, S), threonine (Thr, T), tryptophan (Trp, W), tyrosine (Tyr, Y), and valine (Val, V). Alternatively, any synthetic or commercially available amino acid residue can be used.

Examples of suitable metal coordinating groups include carboxyl, thiol, imidazole, carboxamide, hydroxyl, phenol, thiazole, pyridine, pyrazole, bipyridine, terpyridine, phenanthroline, catechol, hydroxamate and phosphine.

The metal coordinating groups in the peptide can be covalently attached to (1) an amino acid side chain functional group (such as a thiol (e.g. Cys), amine (e.g. β-amino Ala or Lys), carboxylate (e.g. Asp or Glu), hydroxy (e.g. Ser or Thr), etc.), (2) a backbone amide or (3) the carboxylic acid or amine termini of the peptide. In general, groups containing a carboxylic acid, aryl chloride or a sulfonyl chloride group can be incorporated onto the N-terminus of the peptide as the last step in the synthesis. Alternatively, groups can first be incorporated onto the side chain of a residue (for example, onto the amino group of a β-amino alanyl group) or onto the amino group of a residue and subsequently added as a residue during the synthesis of the peptide.

Naturally encoded metal binding amino acids include Cys, Asp, Glu, and His. Examples of synthetic metal binding amino acids include 6-bipyridinyl-alanine (6-Bpa), 5-bipyridinyl-alanine (5-Bpa), 4-bipyridinyl-alanine (4-Bpa), 2-phenanthrolyl-alanine (2-Fen), 5'-amino-2-2'-bipyridine-5-carboxylic acid (ω-Bpa) (Cheng, 1996, supra), Neo (Cheng, 1996, supra), glycyl-5'-amino-2-2'-bipyridine-5-carboxylic acid (XBp); the structures of which are shown below.

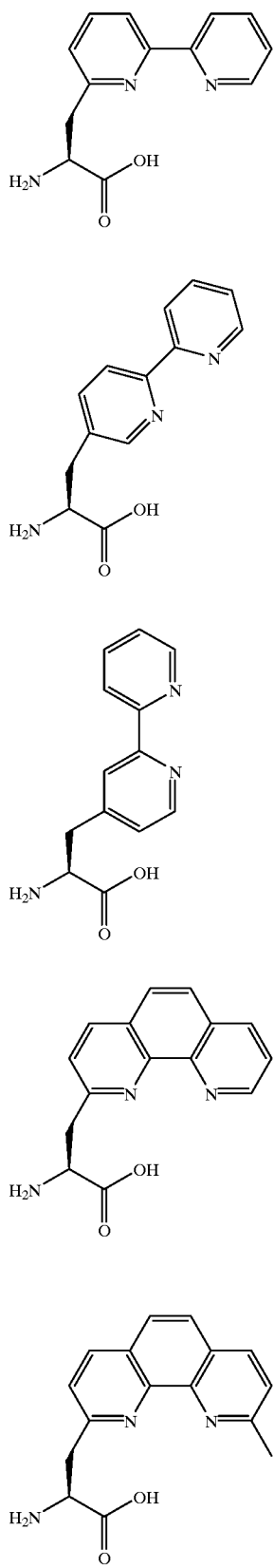

6-Bpa
5-Bpa
4-Bpa
2-Fen
Neo

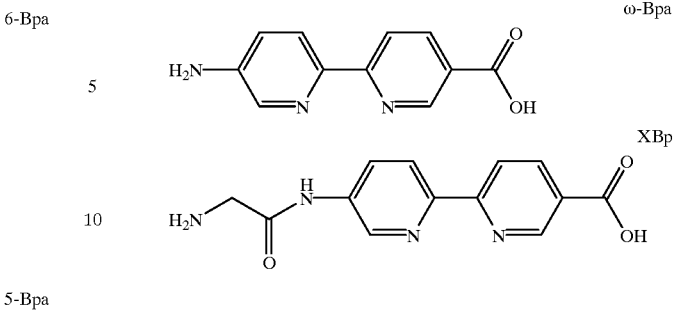

ω-Bpa
XBp

The above metal binding amino acids can be substituted with 1 or more, preferably 1, 2 or 3, substituents selected from the group consisting of halogens (fluorine, chlorine, iodine, bromine), $C_{1-6}$alkanes, $C_{2-6}$alkenes, amines, etc. Aromatic hydrogens are preferably exchanged for one of the above substituents.

Figure 1:
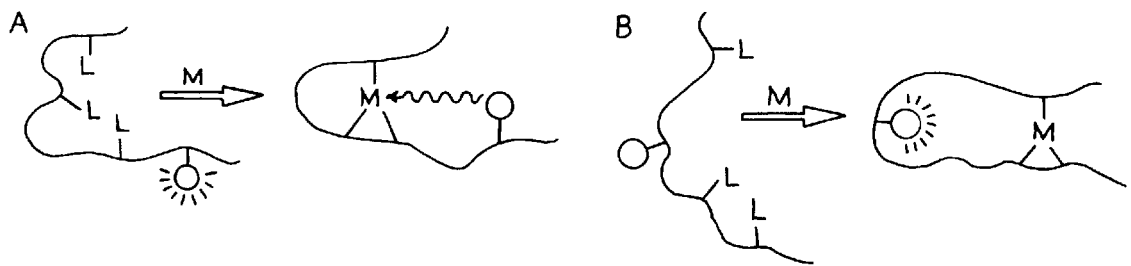
FIG. 1 is an illustration of two sensor designs. (A) Metal coordination brings the fluorophore into proximity with the metal center, allowing intramolecular energy transfer and causing a decrease in fluorescence signal. (B) Metal coordination triggers a change in the fluorophore environment and an increase in the fluorescence signal.

The identity of suitable metal signaling groups, or fluorescent reporter groups, depends on the signaling mechanism to be employed and the metal ion to be detected. In mechanism A (FIG. 1) any fluorescent group which may transfer energy to a bound metal ion with an open shell electronic structure (eg. Ni(II), Co(II), Cu(II), Fe(II), Fe(III), Mn(II)) may be employed. Suitable examples include; 5-dimethylamino naphthalene sulfonamide (DNS) and carboxamido coumarin (CMN). In mechanism B (FIG. 1) any fluorescent group which undergoes a change in photophysical properties upon experiencing a change in the local environment. Suitable examples of metal signaling groups include 5-dimethylamino naphthalene sulfonamide (DNS), p-nitrobenzoxazolidinone (NBD) and anilino-naphthalene sulfonamide (ANS). The above residues can be synthesized as described in the art. For a review see, RP Haugland, "Covalent Fluorescent Probes", In Excited States of Biopolymers, RF Steiner, Ed., Plenum Press: N.Y., 1983; incorporated herein by reference.

1B. Peptide Motifs

As a starting point, peptides which are analogs of proteins which are known to bind metals are used. Alternatively, analogs of peptides that show selective binding to transition metal cations are used. Such sequences will be used as the starting point for screening for new ion-selective chemosensors; however it is to be understood that any peptide which binds a metal and which undergoes a detectable fluorometric perturbation when a metal is bound can be used.

1. B.i. Metal Binding Protein Motifs

For example, zinc finger proteins are known to bind $Zn^{2+}$. The primary amino acid sequences of some zinc finger proteins are included in the databases described by Krizek et al., *J. Am. Chem. Soc.* 1991, 113:4518 and Jacobs, G. H., *EMBO J.* 1992, 11:4507; incorporated herein by reference.

The signaling mechanism involves a single environment-sensitive fluorophore. The zinc finger polypeptides incorporate a tetrahedral divalent zinc binding site, with two imidazole and two thiolate ligands. Zinc finger motifs demonstrate strong affinity ($K_d=10^{-10}$–$10^{-12}$ M) for zinc relative to other early transition metal cations. Binding of $Ni^{II}$, $Co^{II}$ or $Fe^{II}$ to a prototypical zinc finger peptide (Krizek, 1992, supra) produces complexes reminiscent of the native $Zn^{II}$ structure, however, the dissociation constants for these cations are approximately $10^5$ less favorable than for zinc. The selectivity for zinc in this case, which is in sharp contrast to the trends usually observed for "open"

zinc-ligand complexes, can be understood on the basis of ligand field effects (Krizek, B. A. & Berg, J. M., *Inorg. Chem.* 1992, 31:2984; Berg, J. M. & Merkle, D. L., *J. Am. Chem. Soc.* 1989, 111:3759).

The tertiary structure of the zinc finger polypeptides is completely dependent on the structural organization provided by bound zinc, and the polypeptides exist in a disordered state in the absence of metal (Eis, P. S. & Lakowicz, J. R., *Biochemistry* 1993, 32:798 1; Berg, J. M., *Ann. Rev. Biophys. Biophys. Chem.* 1990, 19:405; Berg, J. M. *Curr. Op. Struct. Biol.* 1993, 3:1 1). The structure of the metal-bound domain has been determined by both X-ray and NMR methods and shown to be a compact ββ folded motif (Eis, P. S. & Lakowicz, J. R., *Biochemistry* 1993, 32:798 1; Klevit, R. E., et al., *PROTEINS: Struct. Funct. Genet.* 1990, 7:215; Pavletich, N. P. & Pabo, C. O., *Science* 1991, 252:809; Fairall, L., et al., *Nature* 1993, 366:483). This motif is suitable as a template for the chemosensor design shown in FIG. 1A because metal coordination induces a conformational change that results in the sequestration of specific amino acid side chains into a hydrophobic cluster. The consensus sequence for the zinc finger domains, showing the location of both the metal-ligating and the conserved hydrophobic amino acid residues, is:

B: (Phe/Tyr)-X-Cys-$X_{2-4}$-Cys-$X_3$-Phe-$X_5$-Leu-$X_2$-His-$X_{3-5}$-His-$X_{2-6}$ where X is any naturally encoded amino acid. When one of the hydrophobic residue side chains is replaced with an environment-sensitive fluorophore, a fluorescent signal will accompany metal binding because the micro-environment of the residue has changed.

The emission properties of many fluorophores, including the 1-dimethylamino-8-naphthalene sulfonamide or dansyl group (DNS) and the 6-propionyl-2-(dimethylamino) naphthalene (PRODAN) groups are very sensitive to the polarity of the surrounding medium (Lakowicz, J. R. "Effects of Solvents on Fluorescence Emission," In *Principles of Fluorescence Spectroscopy*; Plenum Press: New York, 1983; pp 189). Therefore amino acids, such as Baa-Dns, that integrate these fluorophores as part of the residue side chain may be employed in this design.

The designed polypeptide ZNS1 (AcTyrGlnCysGlnTyrCysGluLys-ArgBaa(Dns)AlaAspSerSerAsnLeuLysThrHisIleLysThrLysHisSer SEQ ID NO:3 $NH_2$) shows a linear response to $Zn^{II}$ in the 100–1000 nM range. The peptide motif is selective for zinc even in the presence of high levels of other competing divalent species such as $Ca^{II}$ and $Co^{II}$.

1. B.ii. Peptides That Selectively Bind Transition Metal Cations

Short peptides that selectively bind to transition metal cations are known (Mukherjee, G. N. & Chattopadhyay, S. K., *J. Indian Chem. Soc.* 1991, 68:639–642; Hulsbergen, F. B. & Reedijk, J., *Recl. Trav. Chim. Pays-Bas* 1993, 112:278–286; Ama, T., et al., *Bull Chem. Soc. Japan* 1989, 62:3464–3468).

For example, the distinguishing feature of simple $Co^{II}$/ligand complexes (when compared to $Cu^{II}$ and $Ni^{II}$) is the greater tolerance of tetrahedral coordination geometries. Therefore, this structural characteristic can be used to guide the design of polypeptide chemosensors for $Co^{II}$. For example, the simple hexapeptides, including the unnatural amino acid phenanthrolylalanine (Fen) and a histidine (eg. AcFenValProDSerPheHis SEQ ID NO:4 $NH_2$) have been shown to have excellent binding to $Co^{II}$ and $Cu^{II}$ (Cheng, 1996, supra) Through the introduction of softer donor ligands such as the thiolate of cysteine into this simple peptide, the selectivity for $Co^{II}$ over $Cu^{II}$ can be enhance, developing a platform for $Co^{II}$ recognition and sensing.

Figure 2:
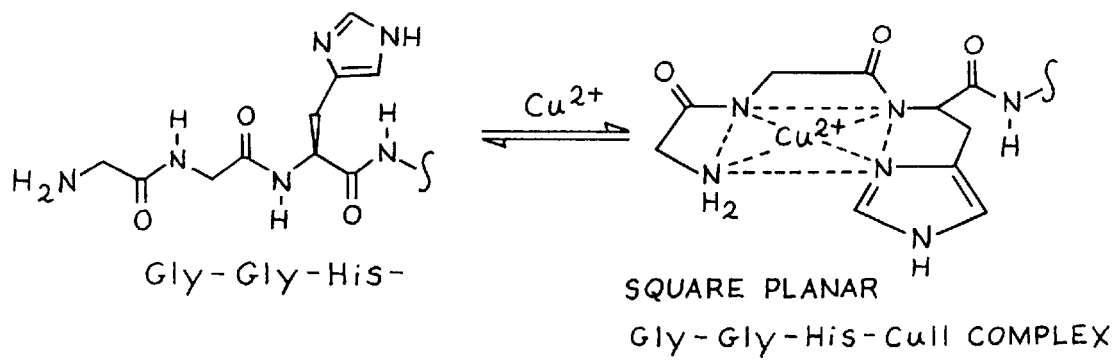
FIG. 2 illustrates binding motif of polypeptides which recognize $Ni^{II}$ and $cu^{II}$ in a 1:1 complex.

The polypeptide motifs for the recognition of $Ni^{II}$ and $Cu^{II}$ can be based on the tripeptide sequence Gly-Gly-His-. This simple sequence mimics the amino-terminal square planar $Cu^{II}$-chelating domain of serum albumins and binds $Cu^{II}$ or $Ni^{II}$ in a 1:1 complex (illustrated in FIG. 2). Example 1 describes a first example of a peptide that selectively binds $N^{II}$ and $C^{II}$. These results establish a firm precedent for the implementation of simple fluorescent peptides as selective metal ion chemosensors. This construct can also be used for the selective recognition of other divalent metal cations. The small relative size and the modular nature of the polypeptide motif makes it a perfect target for combinatorial chemistry and the generation of a broad family of related congeners that may be tested for high specificity towards target analytes. The sites in the molecule that may be permuted to afford different metal-coordinating properties are illustrated below.

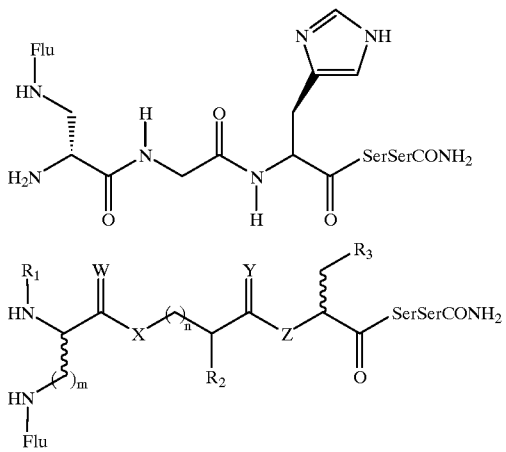

$R_1$; vary amino terminus (eg. primary or secondary amine with different substituents)

$R_2$; vary side chain substituent to modulate steric and electronic effects $R_3$; vary key coordinating ligand )eg. pyridinyl, thiazolyl, thiol, or carboxylic acid)

W and Y; O or S (amide or thioamide)

X and Z; O or NH (ester or amide)

n and m; vary methylene (0–4)

Flu; vary fluorophore to modulate excitation and emission wavelengths

Figure 5:
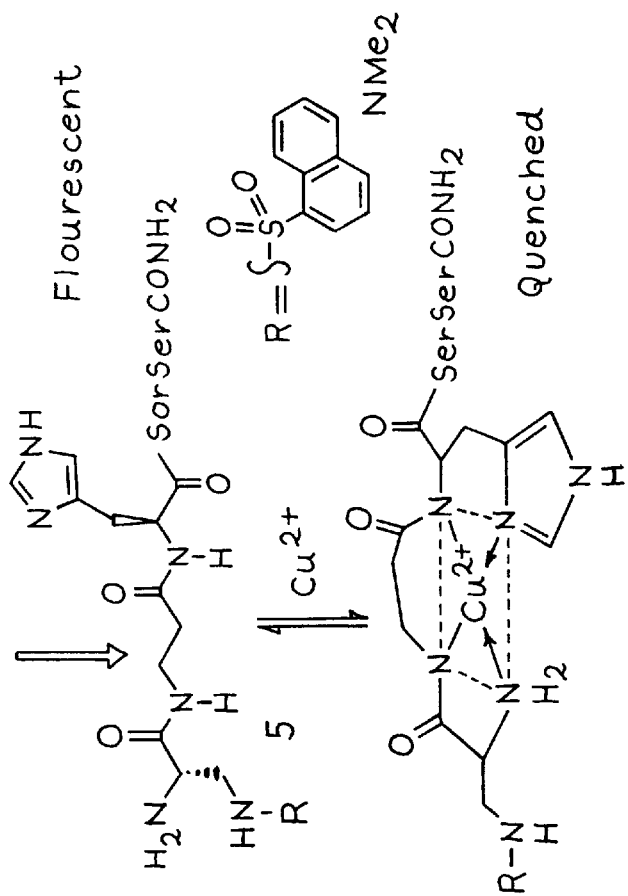
FIG. 5(a) The bar graph highlights $Cu^{II}$ selectivity; (A) 12 μM peptide, 0.15 M NaCl. (B) with $Ca^{II}$, $Mn^{II}$, $Co^{II}$, $Ni^{II}$, $Zn^{II}$, $Fe^{II}$, and $Cd^{II}$. (C) with one equivalent $Cu^{II}$. (b) The $Cu^{II}$ binding isotherm is shown. (c) illustrates the selective recognition of $Cu^{II}$ by the pentapeptide (5) in water.
Figure 5:
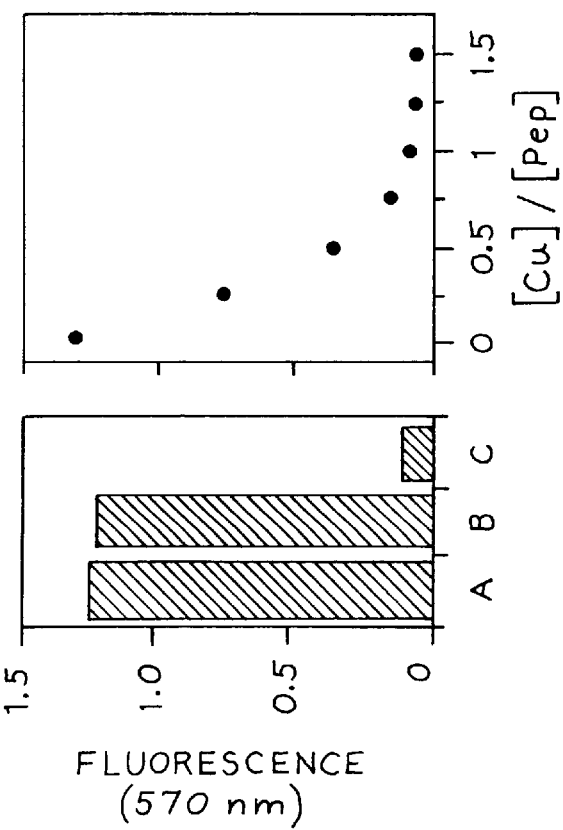

For example the basic motif is known to recognize $Cu^{II}$ and $Ni^{II}$, however, selective thermodynamic binding in each case may be influenced by ion size, donor type, and coordination complex geometry. Since the ionic radii of the transition metal series are similar, the cations can be distinguished based on criteria such as coordination complex geometry and ligand type (hard v. soft). The results disclosed in Example 1 and illustrated in FIG. 5 show how powerful a minor perturbation of complex geometry can be for achieving a particular specificity. Specificity for $Cu^{II}$ has also been achieved by replacing the histidine imidazole with a thiazole ring system at position $R_3$. Additionally, variations in the side chain substituent $R_2$ have been shown to greatly influence $Ni^{II}$ binding. In general, ligand exchange with $Ni^{II}$ is slow, however, addition of carboxylic acid substituted side chain substituents at the $R_2$ position (i.e. by employing aspartic acid, glutamic acid or a homologue) greatly improves the kinetics of complex formation and the potential utility of the motif for the detection of $Ni^{II}$.

1. C. Synthesis of Arrays of Peptide

As used herein, "array of peptides" is a group of peptides physically separated from each other based on their amino acid sequences.

The peptides can be individually synthesized and assembled into arrays. More preferably, the peptides are synthesized in an array using a combinatorial chemical approach.

Parallel arrays of peptides on glass surfaces can be prepared via the light-directed, spatially addressable methodology of Affymax (U.S. Pat. No. 5,143,854; Fodor, S. P. A., et al., *Science* 1991, 251:767–773; Holmes, C. P., et al., *Biopolymers* 20 1995, 37:199–211; incorporated herein by reference). The process relies on the ability to prepare surfaces with a covalently attached amine group that is temporarily blocked with a photolabile protecting group.

Figure 7:
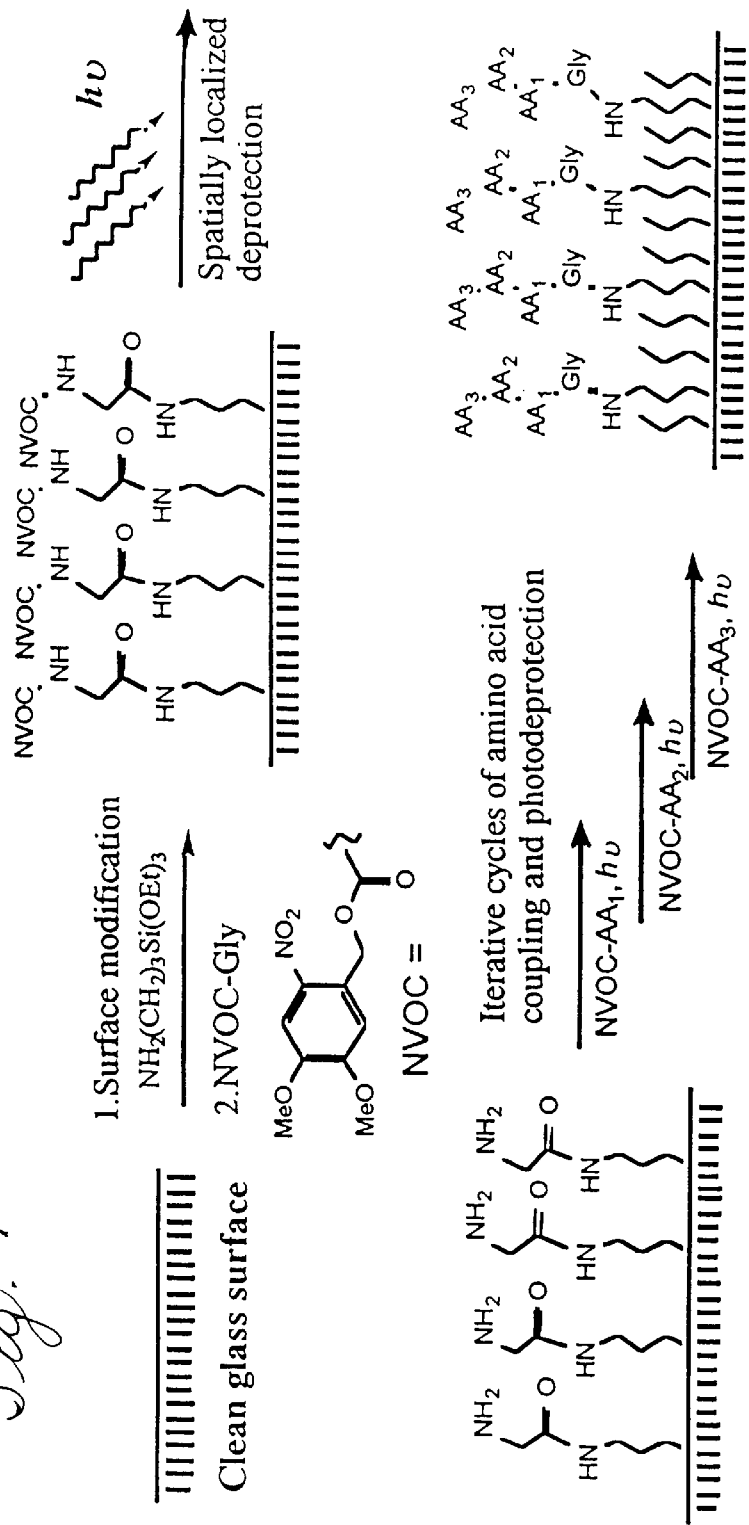
FIG. 7 illustrates the steps of the invention: (1) Clean glass surface according to Ulman, A. *An Introduction to Ultrathin Organic Films from Langmuir-Blodgett to Self-Assembly*; Academic Press: New York, 1991; pp 442; (2) Treat with 3-aminopropyltriethoxysilane according to Sundberg, S. A. *J. Am. Chem. Soc.* 1996, 117:12050–7; (3) Couple to linker (optional); (4) Attach NVOC protected amino acid via standard coupling chemistry; (5) Deprotect photolabile group. Full masking and spatial localization of deprotection described in: Holmes, C. P. et al., *Biopolymers* 1995, 37:199–211 and; Fodor, S. P. A., et al., *Science* 1991, 251:767–773; (6) Repeat steps 4 and 5 until the synthesis of the peptide array is complete; (7) At the conclusion of the synthesis the amino acid side chain protecting groups are removed with a standard trifluoroacetic acid treatment.
Figure 8:
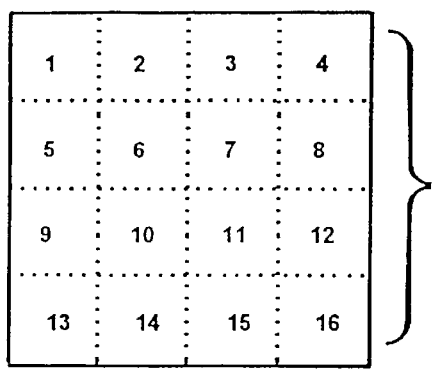
FIG. 8 illustrates a fluorescent detection device for detecting metal binding peptides on a substrate.
Figure 8:
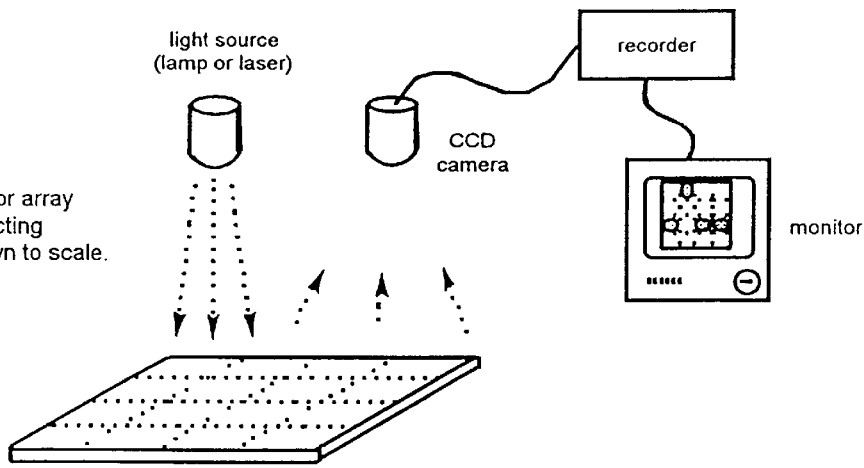
Figure 8:
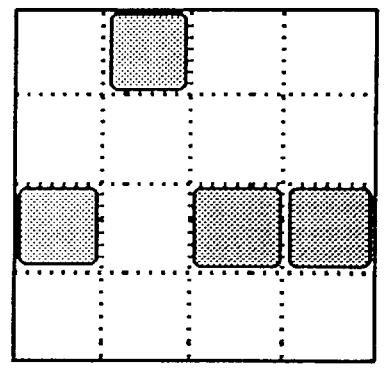

FIG. 7 illustrates this method. Borosilicate microscope coverslips can be prepared for derivatization by soaking for 15 minutes in freshly prepared piranha solution (Ulman, A. *An Introduction to Ultrathin Organic Films from Langmuir-Blodgett to Self-Assembly*; Academic Press: New York, 1991; pp 442). The coverslips are thoroughly washed with deionized water, followed by 95% ethanol/water. The amine handle for peptide synthesis is attached by submerging the coverslips in a solution of 2% v/v (3-aminopropyl) triethoxysilane in 95% ethanol/water for 15 minutes (Sundberg, S. A., et al., *J. Am. Chem. Soc.* 1995, 117:12050–12057). Further elaboration of the amine may be performed immediately following this procedure. This derivatization procedure affords a new surface that is amenable to photolithography for amine deprotection and subsequent iterations of amide bond formation resulting in peptide synthesis. The methodology retains versatility with respect to peptide coupling chemistry. Peptides varying in length from 6–15 residues can be prepared by this chemistry. Matrices of up to 32×32 peptide arrays (1024 different peptides) have actually been prepared using this methodology. The use of arrays allows the construction of increasingly complex (and miniaturized) arrays for the rapid evaluation of a large numbers of peptides.

The array can be formed on any substrate by these methods. In a preferred embodiment, the array is formed on flat glass or single-crystal silicon. A standard glass surface functionalization density is suitable for use with this technology. "Treated" glass surface can be modified with the peptides to provide fluorescent probes. These surfaces provide ample signal for observation using a fluorescence microscope with a CCD attachment for signal intensification.

The surface of the substrate is preferably provided with a layer of linker molecules, although the linker molecules are not required. The linker molecules are preferably of sufficient length to permit polymers in a completed substrate to interact freely with molecules expos/e the substrate. The linker molecules preferably are 6–50 atoms. Suitable examples include aryl acetylene, ethylene glycol oligomers containing 2–10 monomer units, diamines, diacids, amino acids, or combinations thereof Other linker molecules may be used in light of this disclosure.

In an alternative embodiment, linker molecules are also provided with a photocleavable group at an intermediate position. The photocleavable group is preferably cleavable at a wavelength different from the protective group. This enables removal of the various polymers following completion of the synthesis by way of exposure to the different wavelengths of light.

The linker molecules can be attached to the substrate via carbon-carbon bonds using, for example, (poly) trifluorochloroethylene surfaces, or preferably, by siloxane bonds (using, for example, glass or silicon oxide surfaces). Siloxane bonds with the surface of the substrate may be formed via reactions of linker molecules bearing trichlorosilyl groups. The linker molecules may optionally be attached in an ordered array.

The linker molecules and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl (NVOC), 2-nitrobenzyloxycarbonyl (NBOC) or ,-dimethyldimethoxybenzyloxycarbonyl (DDZ) is used.

Suitable photoremovable protective groups are described in, for example, Patchornik, *J. Am. Chem. Soc.* 1970, 92:6333 and Amit et al., *J. Org. Chem.* 1974, 39:192, both of which are incorporated herein by reference.

The positive reactive group is activated or deactivation for reaction with reagents in solution by exposure to UV light, electron beam lithography, x-ray lithography, or any other radiation. For example, a 5-bromo-7-nitro indoline group, when bound to a carbonyl, undergoes reaction upon exposure to light at 420 nm. Alternatively, a cinammate group is a negative light-reactive group.

The linking molecules are exposed to light through a mask using photolithographic techniques of the type known in the semiconductor industry and described in, for example, Sze, VLSI Technology, McGraw-Hill (1983), and Mead et al., Introduction to VLSI Systems. Addison-Wesley (1980), which are incorporated herein by reference.

The light may be directed at either the surface containing the protective groups or at the back of the substrate, so long as the substrate is transparent to the wavelength of light needed for removal of the protective groups. Suitable masks include a transparent support material selectively coated with a layer of opaque material. Portions of the opaque material are removed, leaving opaque material in the precise pattern desired on the substrate surface. The mask is brought into close proximity with, imaged on, or brought directly into contact with the substrate surface. "Openings" in the mask correspond to locations on the substrate where it is desired to remove photoremovable protective groups from the substrate. Alignment may be performed using conventional alignment techniques in which alignment marks are used to accurately overlay successive masks with previous patterning steps, or more sophisticated techniques may be used. For example, interferometric techniques such as the one described in Flanders et al., *App. Phys. Lett.* 1977, 31:426–428, which is incorporated herein by reference, may be used.

The light may be from a conventional incandescent source, a laser, a laser diode, or the like. If non-collimated sources of light are used it is desirable to provide a thick- or multi-layered mask to prevent spreading of the light onto the substrate. Alternatively groups which are sensitive to different wavelengths can be used to control synthesis. For example, by using groups which are sensitive to different wavelengths, it is possible to select branch positions in the synthesis of a polymer or eliminate certain masking steps. Several reactive groups along with their corresponding wavelengths for deprotection are shown below.

| Group | Approximate Deprotection Wavelength (nm) |
|---|---|
| Nitroveratryloxy carbonyl (NVOC) | 300–400 |
| Nitrobenzloxy carbonyl (NBOC) | 300–350 |
| Dimethyl dimethoxybenzyloxy carbonyl | 280–300 |
| 5-Bromo-7-nitroindolinyl | 420 |
| o-Hydroxy- -methyl cinnamoyl | 300–350 |
| 2-Oxymethylene anthraquinone | 350 |

The substrate may be irradiated either in contact or not in contact with a solution and is, preferably, irradiated in contact with a solution. The solution contains reagents to prevent the by-products formed by irradiation from interfering with synthesis of the polymer according to some embodiments. Alternatively, the solution may contain reagents used to match the index of refraction of the substrate. Reagents added to the solution may include acidic or basic buffers, thiols, substituted hydrazines and hydroxylamines, reducing agents (e.g., NADH) or reagents known to react with a given functional group.

Either concurrently with or after the irradiation step, the linker molecules are washed or otherwise contacted with a first amino acid which is N-protected with a photoprotective group. The first amino acid reacts with the activated functional groups of the linkage molecules which have been exposed to light. The photoprotective group on the amino acid may be the same as or different than the protective group used in the linkage molecules, and may be selected from any of the above-described protective groups. Preferred groups include NBOC and NVOC.

The process of irradiating is thereafter repeated, with a mask repositioned so as to remove linkage protective groups and expose functional groups which were protected in the previous masking step. As an alternative to repositioning of the first mask, a second mask will be utilized. Alternatively, some steps may provide for illuminating a common region in successive steps.

A subsequent series of masking and contacting steps similar to those described can be used to provide an array of peptides of differing sequences.

In a less preferred embodiment, the peptides can be synthesized using conventional peptide synthesis techniques (see for example, M. Bodansky, Principles of Peptide Synthesis, Springer-Verlag: Berlin, 1984; Stewart & Young, Solid Phase Peptide Synthesis, Pierce: Rockford Ill., 1984; incorporated herein by reference). Suitable methods solution phase methods and solid phase methods (e.g., Marglin, A. and Merrifield, R. B., *Ann. Rev. Biochem.* 1970, 39:841–866; Erickson, B. W., Merrifield, R. B. in "The Proteins", Vol. 2, 255–257, Academic Press, New York (1976); Meienhofer, J., in "Hormonal Proteins and Peptides", Vol. 2. 45–267, Academic Press, New York (1973)).

For example, a spacer group, such as N-t-butyloxycarbonyl-L-lysine methyl ester, is coupled to a peptide resin, such as polyethylene polyacrylic acid (PPA), via the N-amino group of the side-chain. The couplings can be catalyzed with known peptide coupling agents such as dicyclohexyl carbodiimide (DCC), N-hydroxybenzotriazole (HOBT), etc. Thereafter, a N-protected amino acid group is coupled thereto to form a peptide-like spacer. Successive amino acids are added by deprotecting the protecting group and coupling another N-protected amino acid, etc. At the completion of the final coupling reaction, the N-protecting group can be removed and the terminal amino group optionally can be capped with a fluorescent reporter group or some other capping group (such as an acetic group).

Suitable N-protecting groups are known in the art and include, for example, 9-fluorenylmethyloxycarbonyl (FMOC) and the t-butyloxycarbonyl (Boc). Suitable side chain protecting groups depend on the selected N-protecting groups. Suitable side chain protecting groups for FMOC chemistry include Boc for lysine and His, t-butyl esters for Asp and Glu, t-butyl ethers for Ser, Thr, and Tyr, trityl for Cys, PBF for Arg. Suitable side-chain protecting groups for Boc chemistry include, for example, O-benzyl for Thr, Ser, Asp, Glu and Tyr; carbobenzoxy for Lys; tosyl for Arg; 4-methyl benzyl for Cys and 1-benzyloxycarbonylamido-2, 2,2,-trifluoroethyl for His. Side-chain deprotection can be achieved by treatment with borontris (trifluoracetate) in trifluoreacetic acid for 90 minutes at room temperature (see Pless, J., Bauer, W., *Angewante Chem. Int. Ed. Engl.* 1973, 12:147). It is to be understood that other N-protecting and side-chain protecting groups can be used with this invention.

Once synthesized the peptides can be formed into arrays using known techniques, for example by depositing peptides into individual wells of a titer plate.

1. D. Analyzing Peptides For Metal Binding Properties

An array is then contacted with an aqueous solution of metal ions. Suitable metal ions include $Zn^{2+}$, $Mn2+$, $Fe^{2+}$, $Co^{2+}$, $Cu^{2+}$, $Ni^{2+}$, $Cd^{2+}$ and $Hg^2$. To obtain quantitative metal binding information, the concentration of metal ions is known and typically ranges from 0.1 mM to 1 nM. The chemosensors can detect deviations from these normal concentrations as small as 0.1 mM.

The array is preferably contacted with the biological sample for a time sufficient to saturate each peptide in the array with the metal ion, preferably at least 30 minutes. Thereafter the aqueous solution is washed to remove unbound metal ions.

The array is then scanned to determine how the presence of the metal effected the fluorescence of each peptide. For example, a fiber optic sensor array, such as described by Muller-Ackermann et al. (Analytical Methods & Instrumentation 1995, 2:182–189), can be used to detect changes in the fluorescence of the peptides in accordance with the present invention when contacted with a metal.

2. Novel Chemosensors

In a second embodiment, the present invention provides novel chemosensors which comprise a peptide which coordinates to a metal and a fluorescence sensor.

2. A. Peptides

As defined above, peptides in accordance with the present invention are composed of amino acid residues, at least one metal coordinating group and a fluorescent reporter group (or fluorophore).

2. B. Fluorescence Sensor

The fluorescence sensor comprises a means for energizing the fluorophore such as a laser and a detector suitable for detecting perturbations in the fluorescence emission of the fluorophore. Suitable fluorescence sensors are known in the art. For example, a fiber optic sensor array, such as described by Muller-Ackermann et al. (Analytical Methods & Instrumentation 1995, 2:182–189), can be used.

By counting the number of photons generated in a given area in response to the laser, it is possible to determine where metal bound peptides are located on the substrate. Consequently, for a slide which has a matrix of polypeptides, for example, synthesized on the surface thereof, it is possible to determine which of the peptides binds a metal.

According to preferred embodiments, the intensity and duration of the light applied to the substrate is controlled by varying the laser power and scan stage rate for improved signal-to-noise ratio by maximizing fluorescence emission and minimizing background noise.

3. Methods for Detecting the Presence of a Metal in a Sample

In a third embodiment, the method of the present invention comprises:

contacting an immobilized chemosensor with a sample, irradiating and measuring the fluorescent emission of said sample, and determining the concentration of metal in said sample based on said fluorescent emission.

In practice, the measurement of the fluorescent emission of said sample will be evidenced by a modulation of the fluorescent signal relative to the background signal. For sensors of Mechanism type A (FIG. 1) the fluorescence would be decreased. For sensors of Mechanism type B (FIG. 1) the fluorescence would be increased.

Figure 6:
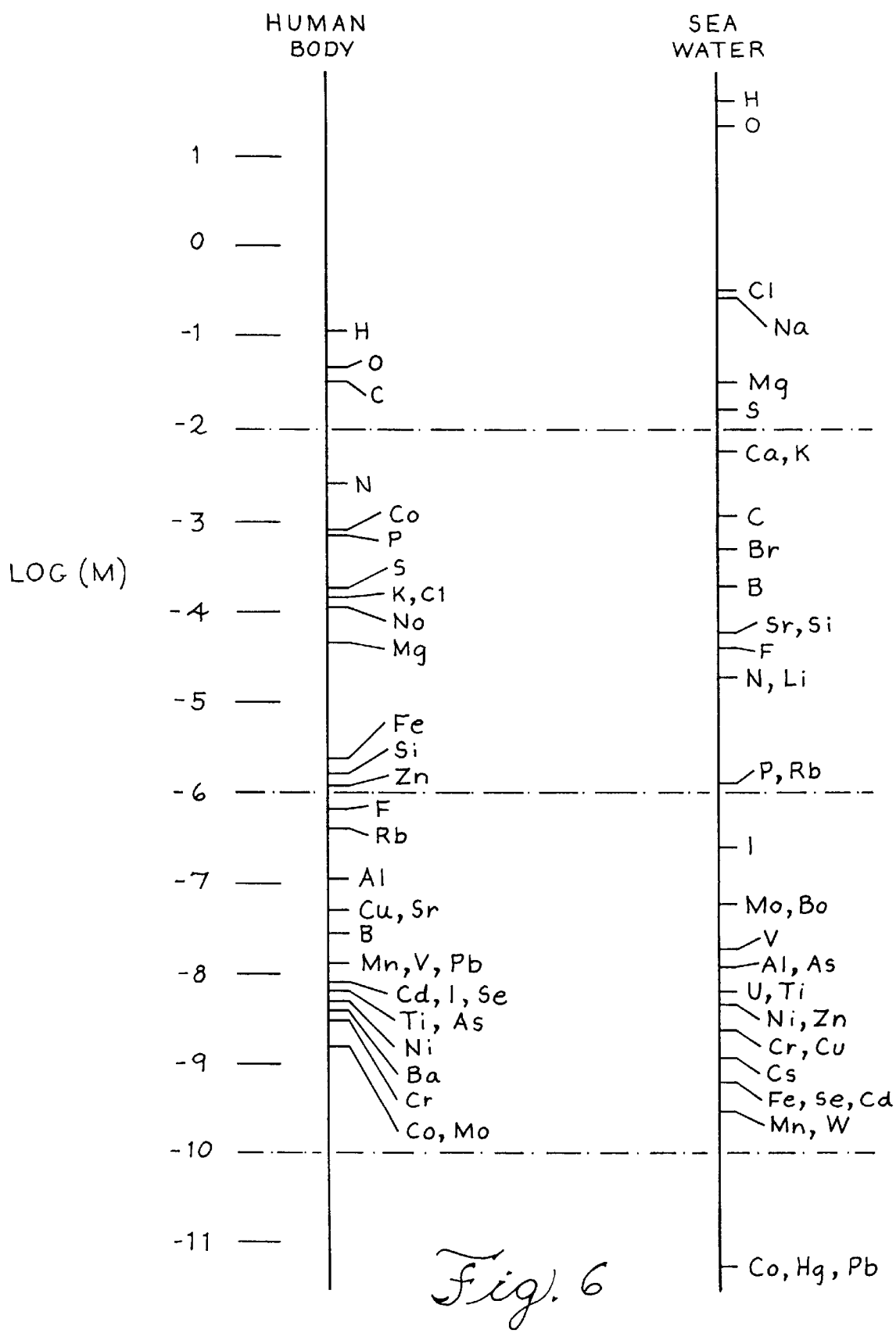
FIG. 6 is a graph depicting the concentration of trace elements in sea water and the human body.

Suitable aqueous solutions can be either biological (such as blood or urine, etc.) or environmental (such as sea water, ground water, etc.). For example, the normal concentrations of metals in seawater and the human body are shown in FIG. 6.

The signal-to-noise ratio of the present invention is sufficiently high that not only can the presence or absence of a metal bound to a peptide be detected, but also the relative binding affinity of metals to a variety of sequences can be determined.

In practice it is found that a metal will bind to several peptide sequences in an array, but will bind much more strongly to some sequences than others. Strong binding affinity will be evidenced herein by a strong fluorescent or radiographic signal since many metal molecules will bind in a region containing a peptide which binds strongly to the metal. Conversely, a weak binding affinity will be evidenced by a weak fluorescent or radiographic signal due to the relatively small number of metal molecules which bind in a particular region of a substrate having a peptide with a weak binding affinity for the metal. Consequently, it becomes possible to determine relative binding affinity of a peptide herein by way of the intensity of a fluorescent signal in a region containing that peptide.

Semiquantitative data on affinities might also be obtained by varying washing conditions and concentrations of the metal. This would be done by comparison to a known metal binding peptide, for example.

Having generally described this invention, a further understanding can be obtained by reference to certain specific examples which are provided herein for purposes of illustration only and are not intended to be limiting unless otherwise specified.

EXAMPLES

Example 1

Development of a selective chemosensor for $Ni^{II}$ and $Cu^{II}$

The polypeptide motifs for the recognition of $N^{II}$ and $Cu^{II}$ were based on the tripeptide sequence Gly-Gly-His-. This simple sequence mimics the amino-terminal square planar $Cu^{II}$-chelating domain of serum albumins and binds $Cu^{II}$ or $N^{II}$ in a 1:1 complex (illustrated in FIG. 2). The ligands in these complexes include the histidine imidazole (δ)-nitrogen, two deprotonated amide nitrogens, and the terminal -amine. The $Cu^{II}$ complex has a dissociation constant on the order of $10^{-16}$–$10^{-17}$ M at neutral pH. Crystallographic analysis of $[Cu^{II}(Gly-Gly-His-NHMe)]$ has confirmed this mode of binding (Camerman, N., et al., Can. J. Chem. 1976, 54:1309).

While the structure of the corresponding $Ni^{II}$ complex has not yet been determined, potentiometric studies have shown that $[Ni^{II}(Gly-Gly-His-)]$ is the major species present in mM aqueous solutions of $Ni^{II}$ and Gly-Gly-His- at pH 7 (Hay, R. W., et al., J. Inorg. Biochem. 1993, 52:17). The remarkable affinity of this tripeptide sequence for selected transition metal cations indicates that it is useful as the basis for the design of chemosensors for $Ni^{II}$ and $Cu^{II}$, if a method for signal transduction could be integrated with the metal-coordinating event. The nature of the transition metals targeted by this motif suggests that intramolecular fluorescence quenching of a suitably appended fluorophore would represent a convenient method for signaling metal ion binding. Since the terminal amine functionality in the Gly-Gly-His tripeptide plays a central role in the coordination of metal ions, the incorporation of Gly-Gly-His is limited to the amino-terminus of polypeptide structures. However, this limitation can be circumvented if an amino acid with a side chain amino functionality is incorporated into the peptide in place of the terminal glycine residue (Shullenberger, D. F., et al., J Am. Chem. Soc. 1993, 115:11038–11039). Furthermore, this side chain functionality of the terminal residue provides a handle for derivatization and the integration of a fluorophore for signal transduction.

Figure 3:
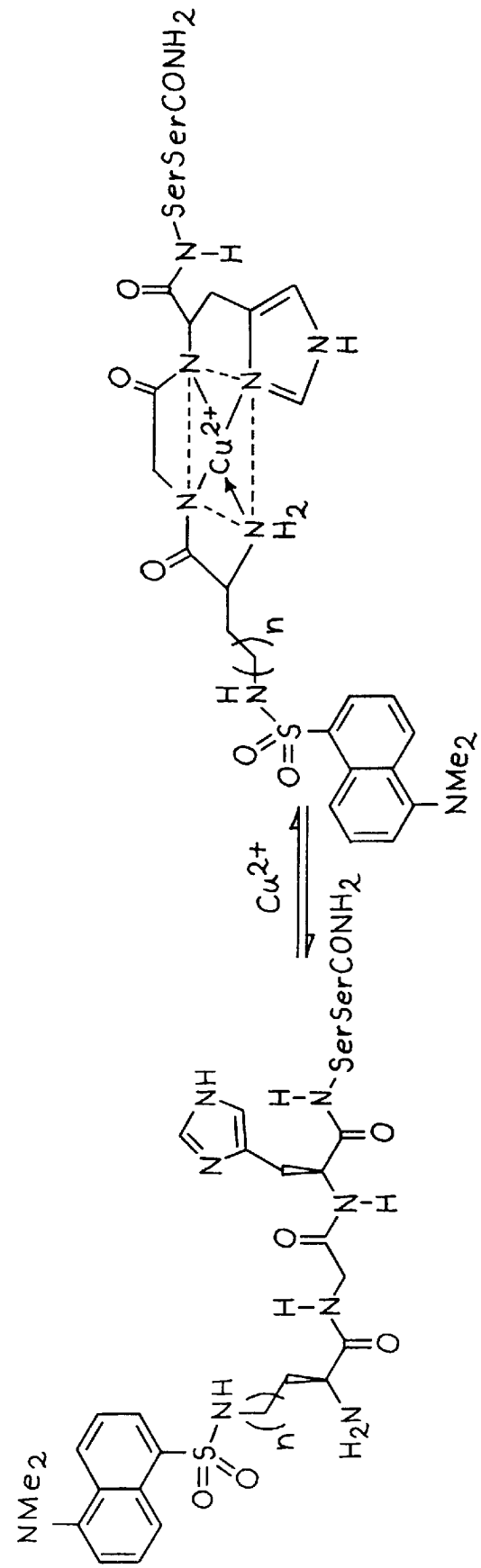
FIG. 3 illustrates a family of pentapeptides (peptides 1–4) which contain analogs of the metal-coordinating tripeptide sequence and a functionalized amino terminal residue through which a dansyl (DNS) fluorophore can be attached.

A family of pentapeptides which contain analogs of the metal-coordinating tripeptide sequence and a functionalized amino terminal residue through which the dansyl fluorophore can be attached (peptides 1–4, FIG. 3) were prepared. In these peptides, the -amino group of the terminal residue remains free to participate in metal ion complexation. The peptide design also included two serine residues to ensure solubility in aqueous test solutions. The first generation of peptides selected for analysis differed only in the length of the methylene chain to which the dansyl fluorophore was attached.

The peptides for this analysis were readily prepared by conventional solid-phase peptide synthesis (SPPS) techniques. The integrity of the purified peptides was confirmed by mass spectroscopy. Fluorescence measurements for these and all later samples containing the dansyl group were obtained by excitation at 333 nm, followed by observation of the emission centered between 550–580 nm. Measurements were made using a 10 μM solution of peptide in 50 mM HEPES, 150 mM NaCl (pH 7.0). The peptide concentrations were calculated based on UV absorption (λ=330 nm, $\epsilon_{max}$=3300$M^{-1}cm^{-1}$).

Figure 4:
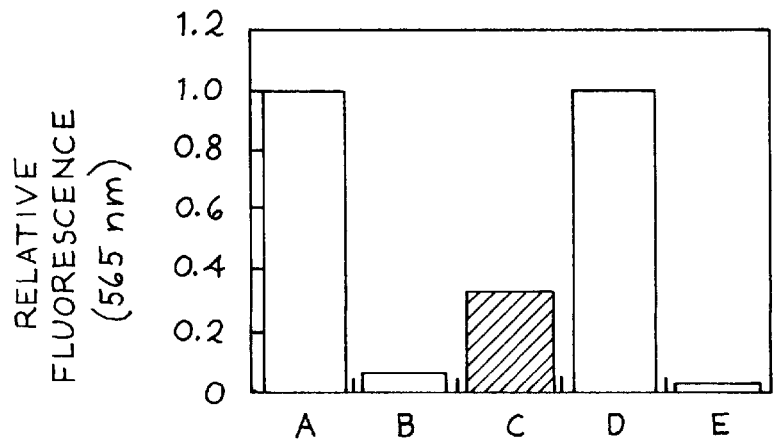
FIG. 4 is a bar graph depicting the residual emission at 570 nm of peptide $2/Cu^{II}$ complex and a peptide $4/Cu^{II}$ complex. (A) Orn(Dns)GlyHisSerSer SEQ ID NO:1 $CONH_2$ (2); (B) 2+1.3 eq $Cu^{II}$; (C) 2+1 eq $Ni^{III}$; (D) Baa(Dns)GlyHisSerSer SEQ ID NO:2 $CONH_2$ (4); (E) 4+1 eq $Cu^{II}$.

Spectroscopic studies with peptides 1–4 show that dansyl fluorescence was quenched upon complexation with one equivalent of $C^{II}$. Further, addition of the chelating agent EDTA resulted in a complete recovery of fluorescence intensity demonstrating that complex formation is reversible and verifying that quenching occurs exclusively via an intramolecular process. The comparative fluorescence studies showed that quenching is most efficient with the shortest spacer between the fluorophore and the metal ion center (peptide 4). For example, residual emission at 570 nm was observed with the peptide 2/$Cu^{II}$ complex, while quantitative quenching was achieved with the peptide 4/$Cu^{II}$ complex (see FIG. 4). Studies with $Ni^{II}$ reveal that while the binding of this divalent cation was slow (relative to $Cu^{II}$), the motif complexed both $Ni^{II}$ and $C^{II}$. In contrast, the fluorescence of these peptides does not change upon the addition of a variety of other divalent cations (eg. $Ca^{II}$, $Mn^{II}$, $Co^{II}$, $Zn^{II}$, and $Cd^{II}$) nor does the presence of these cations interfere with $Cu^{II}$ binding and fluorescence quenching in competition experiments. These studies showed that this small motif selectively signaled the presence of a subset of the transition metal cations.

While peptide 4 demonstrated effective signaling of divalent copper, additional variants of the GlyGlyHis- motif were prepared, including the pentapeptide Baa(dansyl)-β-Ala-His-Ser-Ser SEQ ID NO:5 $CONH_2$ (peptide 5) to establish that the motif could be adapted to be selective for copper over nickel.

These studies resulted in the discovery of a chemo sensor peptide that is selective for $Cu^{II}$ in the presence of a variety of analytes including divalent nickel. The coordination preferences of $Cu^{II}$ and $Ni^{II}$ appear to show subtle variations particularly with respect to coordination geometry; divalent nickel shows a strong preference for square planar complexes, while $Cu^{II}$ manifests less stringent geometrical preferences. A distinct advantage of this simple pentapeptide system is that a number of variants can be readily prepared and screened. Peptide 5, in which the central glycine residue is replaced with a β-amino alanine was completely selective for $Cu^{II}$ over $Ni^{II}$. This modulation in selectivity may be attributed to the fact that peptide 5 no longer provides ligands for an ideal square planar complex. These studies demonstrate that the cross-reactivity with divalent nickel, which is evident in the parent Gly-Gly-His- tripeptide, has been totally eliminated through manipulation of the coordination sphere (FIG. 5).

To demonstrate how an array of peptides could be screened, peptide 5 was prepared by solid phase synthesis onto a non-hydrolyzable linker to the hydrophilic Tentagel . The non-hydrolyzable linker allows peptide assembly from C-terminus to N-terminus under standard conditions. Following completion of peptide assembly and fluorophore derivatization, the side chain protecting groups were removed under acidic conditions, leaving the peptide immobilized on the polymeric support. Therefore, while the linker and resin replace the primary carboxamide in 5, the metal-coordinating components of the motif are unperturbed. Simple fluorescence studies with the peptide-modified Tentagel showed that screening for metal-ion induced fluorescence quenching could be readily assessed even by visual analysis of the resin when illuminated with UV light. The presence of $Cu^{II}$ was determined in the sample, since it showed fluorescence quenching.

Having now fully described the invention, it will be apparent to one of ordinary skill in the art that many changes and modifications can be made thereto without departing from the spirit or scope of the invention as set forth herein.

What is claimed is:

1. A method of screening peptides to determine if any one peptide coordinates to a metal, comprising the steps of:
   (a) contacting an array of peptides with a solution containing a known concentration of a metal;
   wherein said array comprises a plurality of peptides coupled to a solid phase such that peptides of differing amino acid sequence are spatially separated from one another,
   wherein each of said peptides comprising a sequence of at 6–15 amino acid residues and at least one metal binding group or metal signaling group and wherein one of said peptides may bind a metal and undergo a detectable fluorometric perturbation; and
   (b) monitoring the fluorescence of each of the peptides in the array;
   wherein a change in the fluorescence of any one of the peptides is indicative that that peptide coordinates to the metal.

2. The method of claim 1, wherein said metal is $Zn^{2+}$, $Mn^{2+}$, $Fe^{2+}$, $Co^{2+}$, $Cu^{2+}$, $Ni^{2+}$, $Cd^{2+}$ or $Hg^{2+}$.

3. The method of claim 1, wherein said metal coordinating group is carboxyl, thiol, imidazole, carboxamide, hydroxyl, phenol, thiazole, pyridine, pyrazole, bipyrididine, terpyridine, phenanthroline, catechol, hydroxamate or phosphine.

4. The method of claim 1, wherein said solid phase is glass.

5. The method of claim 1, wherein the metal binding group is a metal binding amino acid selected from the group consisting of Cys, Asp, Glu, His, 6-bipyridinyl-alanine, 5-bipyridinyl-alanine, 4-bipyridinyl-alanine, 2-phenanthrolyl-alanine, 5'-amino-2-2'-bipyridine-5-carboxylic acid, glycyl-5'-amino-2-2'-bipyridine-5-carboxylic acid and:

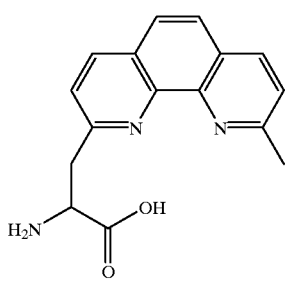

6. The method of claim 1, wherein said known concentration of the metal is from 0.1 mM to 1 nM.

7. The method of claim 1, wherein said metal signaling group transfers energy to bound metal ions.

8. The method of claim 7, wherein said metal signaling group is 5-dimethylamino naphthalene sulfonamide (DNS) or carboxamido coumarin (CMN).

9. The method of claim 1, wherein said metal signalling group undergoes a change in photophysical properties when there is a change in the local environment.

10. The method of claim 9, wherein said metal signaling group is 5-dimethylamino naphthalene sulfonamide (DNS), p-nitrobenzoxazolidinone (NBD) or anilino-naphthalene sulfonamide (ANS).

* * * * *

UNITED STATES PATENT AND TRADEMARK OFFICE
CERTIFICATE OF CORRECTION

PATENT NO. : 6,083,758
DATED : July 4, 2000
INVENTOR(S) : Barbara Imperiali et al.

It is certified that error appears in the above-identified patent and that said Letters Patent is hereby corrected as shown below:

Column 1, Title page,
Lines 2-3, under "OTHER PUBLICATIONS", change "Combinatorial Lobraries", to -- Combinatorial Libraries," --.
Line 3, change "J. of Med. Chem." to -- *J. of Med. Chem.* --.
Line 7, under "OTHER PUBLICATIONS", change "Sensor", Angew. Chem. Int. Ed. Eng.," to -- Sensor," *Angew. Chem. Int. Ed. Eng.,* --.
Line 10, under "OTHER PUBLICATIONS", change "Ions", Angew. Chem. Int. Ed. Engl." to -- Ions," *Angew. Chem. Int. Ed. Eng.* --.

Column 2,
Line 3, change "nisms", Chem. Eur. J." to -- nisms," *Chem. Eur. J.* --.
Line 12, change "Grynkiewica" to -- Grynkiewicz --.
Lines 24-25, change ""Fluorescent Chemosensors for Ion and Molecular Recognition"," to -- *Fluorescent Chemosensors for Ion and Molecular Recognition,* --.
Line 25, change "Czamik," to -- Czarnik, --.
Line 31, change "R.B;" to -- R. B.; --.

Page 2, column 1,
Line 4, under "OTHER PUBLICATIONS", change "Luminsecence-based" to -- Luminescence-based --.
Line 13, change "chem." to -- *Chem* --.
Line 30, change, complexes" to -- Complexes --.

Page 2, Column 2,
Line 9, change "Horvath" to -- Horvath, --.

Line 30, change "Kawagughi" to -- Kawagughi, H., --.

UNITED STATES PATENT AND TRADEMARK OFFICE
CERTIFICATE OF CORRECTION

PATENT NO.    : 6,083,758
DATED         : July 4, 2000
INVENTOR(S)   : Barbara Imperiali et al.

It is certified that error appears in the above-identified patent and that said Letters Patent is hereby corrected as shown below:

Claim 1,
Line 7, change "sequence" to -- sequences --.
Line 8, change "," (comma) to -- ; -- (semicolon).
Line 9, change "of at" to -- of --.

Claim 9,
Line 1, change "signalling" to -- signaling --.

Signed and Sealed this

Twenty-seventh Day of November, 2001

Attest:

*Attesting Officer*

NICHOLAS P. GODICI
*Acting Director of the United States Patent and Trademark Office*

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: artificial
      peptide
<220> FEATURE:
<221> NAME/KEY: MOD_RES
<222> LOCATION: (1)
<223> OTHER INFORMATION: X; Orn(dansyl)

<400> SEQUENCE: 1

Xaa Gly His Ser Ser
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: artificial
      peptide
<220> FEATURE:
<221> NAME/KEY: MOD_RES
<222> LOCATION: (1)
<223> OTHER INFORMATION: X; Baa

<400> SEQUENCE: 2

Xaa Gly His Ser Ser
 1               5

```
<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: artificial
      peptide
<220> FEATURE:
<221> NAME/KEY: MOD_RES
<222> LOCATION: (10)
<223> OTHER INFORMATION: X;Orn(dansyl)

<400> SEQUENCE: 3

Tyr Gln Cys Gln Tyr Cys Glu Lys Arg Xaa Ala Asp Ser Ser Asn Leu
 1               5                  10                  15

Lys Thr His Ile Lys Thr Lys His Ser
            20                  25

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: artificial
      peptide
<220> FEATURE:
<221> NAME/KEY: MOD_RES
<222> LOCATION: (1)
<223> OTHER INFORMATION: X;fenanthrolyl alanine

<400> SEQUENCE: 4

Xaa Val Pro Asp Ser Phe His
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: artificial
      peptide
<220> FEATURE:
<221> NAME/KEY: MOD_RES
<222> LOCATION: (1)
<223> OTHER INFORMATION: X;Baa (Dansyl)

<400> SEQUENCE: 5

Xaa Ala His Ser Ser
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: artificial
      peptide

<400> SEQUENCE: 6

Lys Gly His Ser Ser
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: artificial
```

-continued

```
            peptide
<220> FEATURE:
<221> NAME/KEY: MOD_RES
<222> LOCATION: (1)
<223> OTHER INFORMATION: Orn

<400> SEQUENCE: 7

Xaa Gly His Ser Ser
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: artificial
            peptide
<220> FEATURE:
<221> NAME/KEY: MOD_RES
<222> LOCATION: (1)
<223> OTHER INFORMATION: x;Amb

<400> SEQUENCE: 8

Xaa Gly His Ser Ser
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: artificial
            peptide
<220> FEATURE:
<221> NAME/KEY: MOD_RES
<222> LOCATION: (1)
<223> OTHER INFORMATION: x;Baa

<400> SEQUENCE: 9

Xaa Gly His Ser Ser
 1               5
```